United States Patent
Ho et al.

(10) Patent No.: US 6,723,112 B2
(45) Date of Patent: Apr. 20, 2004

(54) BIOACTIVE THREE LOOP COIL

(75) Inventors: Hanh Ho, San Jose, CA (US); Kenneth W. Quan, Jr., San Jose, CA (US); Clifford Teoh, Los Altos, CA (US); Robert M. Abrams, Encinitas, CA (US); Joseph C. Eder, Los Altos Hills, CA (US); Paul C. Slaikeu, San Carlos, CA (US); Michael P. Wallace, Fremont, CA (US); James Barry, Marlborough, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 227 days.

(21) Appl. No.: 09/828,452

(22) Filed: Apr. 6, 2001

(65) Prior Publication Data

US 2001/0034531 A1 Oct. 25, 2001

Related U.S. Application Data

(63) Continuation-in-part of application No. 09/352,188, filed on Jul. 12, 1999, now Pat. No. 6,231,590, which is a continuation-in-part of application No. 09/189,540, filed on Nov. 10, 1998, now Pat. No. 6,187,024.

(51) Int. Cl.$^7$ ............................................. A61M 29/00
(52) U.S. Cl. ................... 606/191; 606/198; 606/194
(58) Field of Search .......................... 606/194, 200, 606/191

(56) References Cited

U.S. PATENT DOCUMENTS

| | | | |
|---|---|---|---|
| 3,847,652 A | 11/1974 | Fletcher et al. | 117/93.1 |
| 4,638,803 A | 1/1987 | Rand | 128/325 |
| 4,739,768 A | 4/1988 | Engelson | 128/658 |
| 4,994,069 A | 2/1991 | Ritchart et al. | 606/191 |
| 5,037,377 A | 8/1991 | Alonso | 600/36 |
| 5,122,136 A | 6/1992 | Guglielmi et al. | 606/32 |
| 5,226,911 A | 7/1993 | Chee et al. | 606/191 |
| 5,234,437 A | 8/1993 | Sepetka | 606/108 |
| 5,250,071 A | 10/1993 | Palermo | 606/198 |
| 5,261,916 A | 11/1993 | Engelson | 606/108 |
| 5,304,194 A | 4/1994 | Chee et al. | 606/191 |
| 5,304,195 A | 4/1994 | Twyford et al. | 606/191 |
| 5,310,407 A | 5/1994 | Casale | 604/51 |
| 5,312,415 A | 5/1994 | Palermo | 606/108 |
| 5,350,397 A | 9/1994 | Palermo et al. | 606/200 |
| 5,354,295 A | 10/1994 | Guglielmi et al. | 606/32 |
| 5,382,259 A | 1/1995 | Phelps et al. | 606/151 |
| 5,383,897 A | 1/1995 | Wholey | 606/213 |
| 5,403,278 A | 4/1995 | Ernst et al. | 604/60 |
| 5,536,274 A | 7/1996 | Neuss | 623/1 |
| 5,554,181 A | 9/1996 | Das | 623/1 |
| 5,607,445 A | 3/1997 | Summers | 606/198 |

(List continued on next page.)

FOREIGN PATENT DOCUMENTS

| | | |
|---|---|---|
| DE | 196 47 280 | 10/1997 |
| WO | WO 98/367784 | 8/1998 |
| WO | WO 99/05977 | 2/1999 |
| WO | WO 99/07294 | 2/1999 |
| WO | WO 99/08607 | 2/1999 |
| WO | WO 99/62432 | 12/1999 |
| WO | WO 00/32112 | 6/2000 |
| WO | WO 00/74577 A1 | 12/2000 |

*Primary Examiner*—Gary Jackson
(74) *Attorney, Agent, or Firm*—Westman, Champlin & Kelly, P.A.

(57) ABSTRACT

One aspect of the present invention pertains to an implantable medical device for at least partially obstructing a neck portion of a vascular aneurysm. The device includes an occlusion subassembly comprising a base section and at least one lateral protrusion fixedly attached to the base section. A therapeutic agent is disposed upon at least one portion of at least one lateral protrusion.

30 Claims, 6 Drawing Sheets

U.S. PATENT DOCUMENTS

| | | | |
|---|---|---|---|
| 5,624,461 A | 4/1997 | Mariant | 606/191 |
| 5,639,277 A | 6/1997 | Mariant et al. | 606/191 |
| 5,643,318 A | 7/1997 | Tsukernik et al. | |
| 5,645,082 A | 7/1997 | Sung et al. | 128/897 |
| 5,645,558 A | 7/1997 | Horton | 606/191 |
| 5,649,949 A | 7/1997 | Wallace et al. | 606/191 |
| 5,658,308 A | 8/1997 | Snyder | 606/191 |
| 5,669,931 A | 9/1997 | Kupiecki et al. | 606/191 |
| 5,690,666 A | 11/1997 | Berenstein et al. | 606/191 |
| 5,690,671 A | 11/1997 | McGurk et al. | 606/200 |
| 5,718,711 A | 2/1998 | Berenstein et al. | 606/191 |
| 5,725,567 A | 3/1998 | Wolff et al. | 623/1 |
| 5,749,894 A | 5/1998 | Engelson | 606/213 |
| 5,824,049 A | 10/1998 | Ragheb et al. | 623/1 |
| 5,837,008 A | 11/1998 | Berg et al. | 623/1 |
| 5,935,148 A | 8/1999 | Villar et al. | 606/213 |
| 5,976,126 A | 11/1999 | Guglielmi | 606/32 |
| 5,980,550 A | 11/1999 | Eder et al. | 606/191 |
| 6,063,104 A | 5/2000 | Villar et al. | 606/213 |
| 6,086,577 A | 7/2000 | Ken et al. | 606/1 |
| 6,187,024 B1 | 2/2001 | Boock et al. | 606/191 |

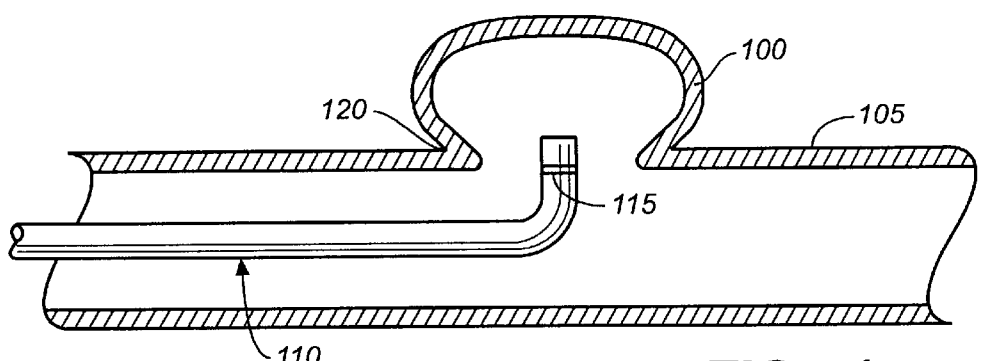
FIG._1
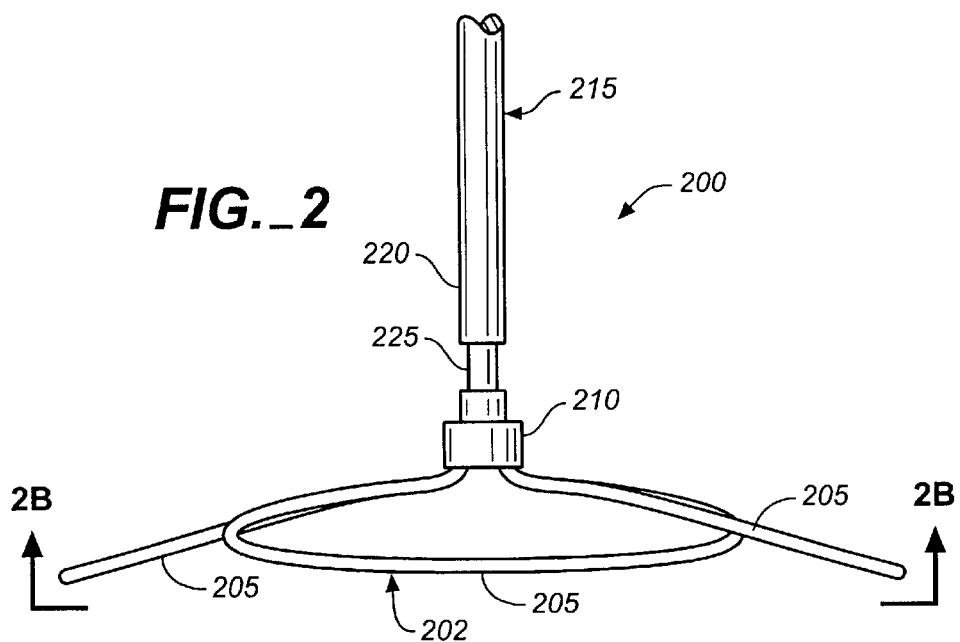
FIG._2
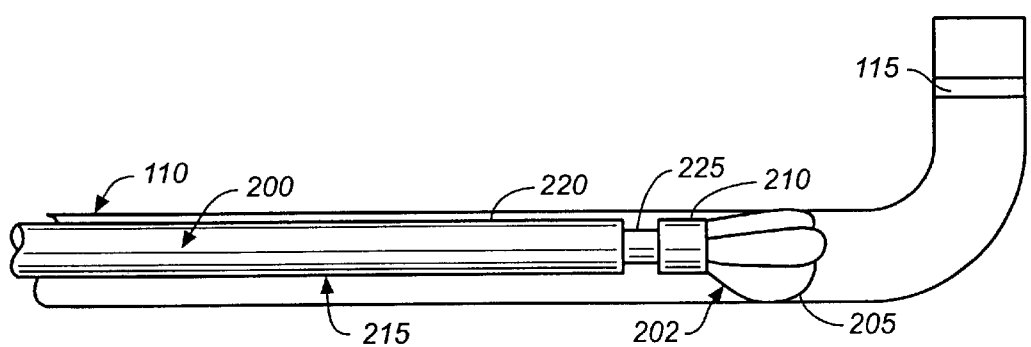
FIG._3

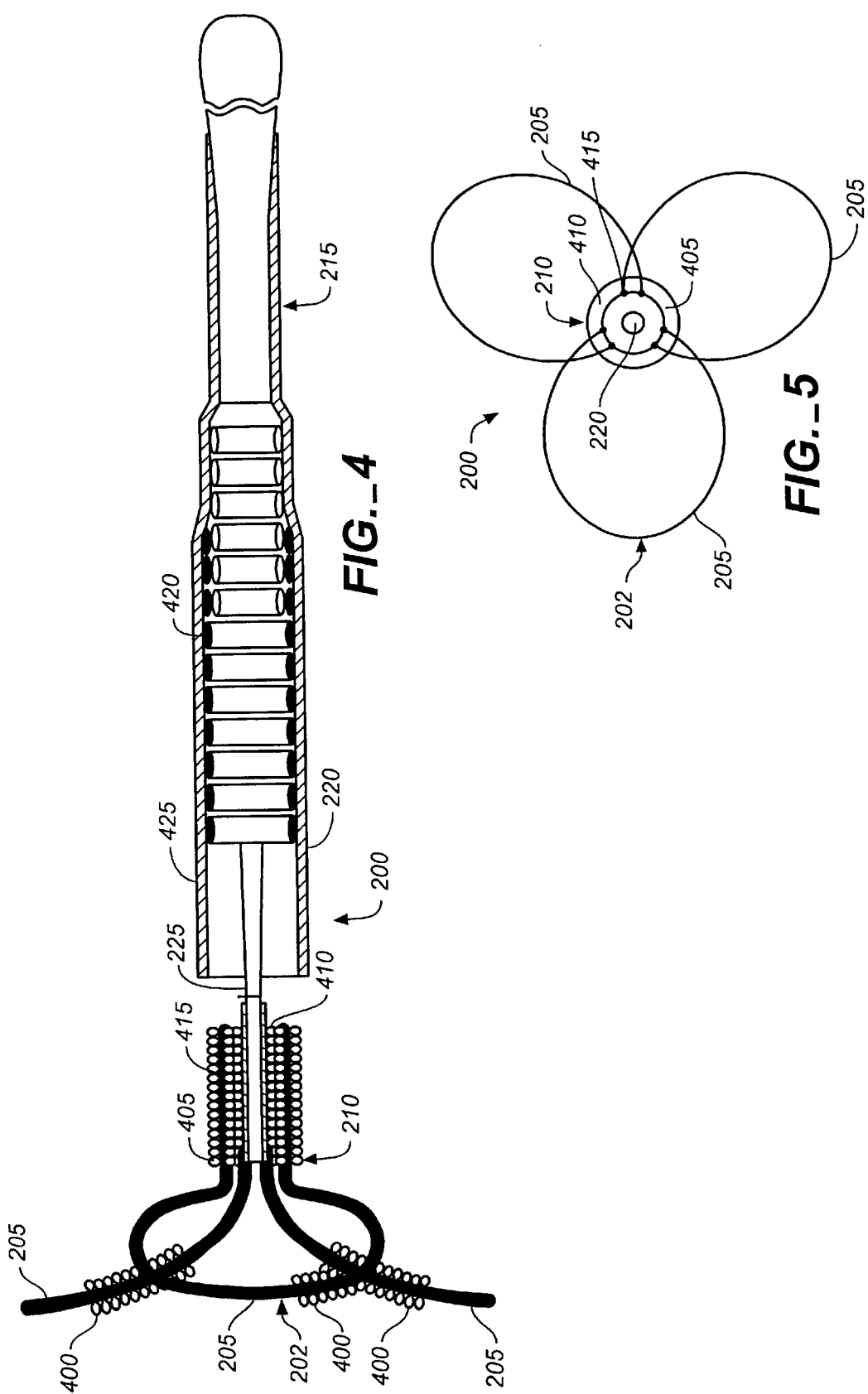

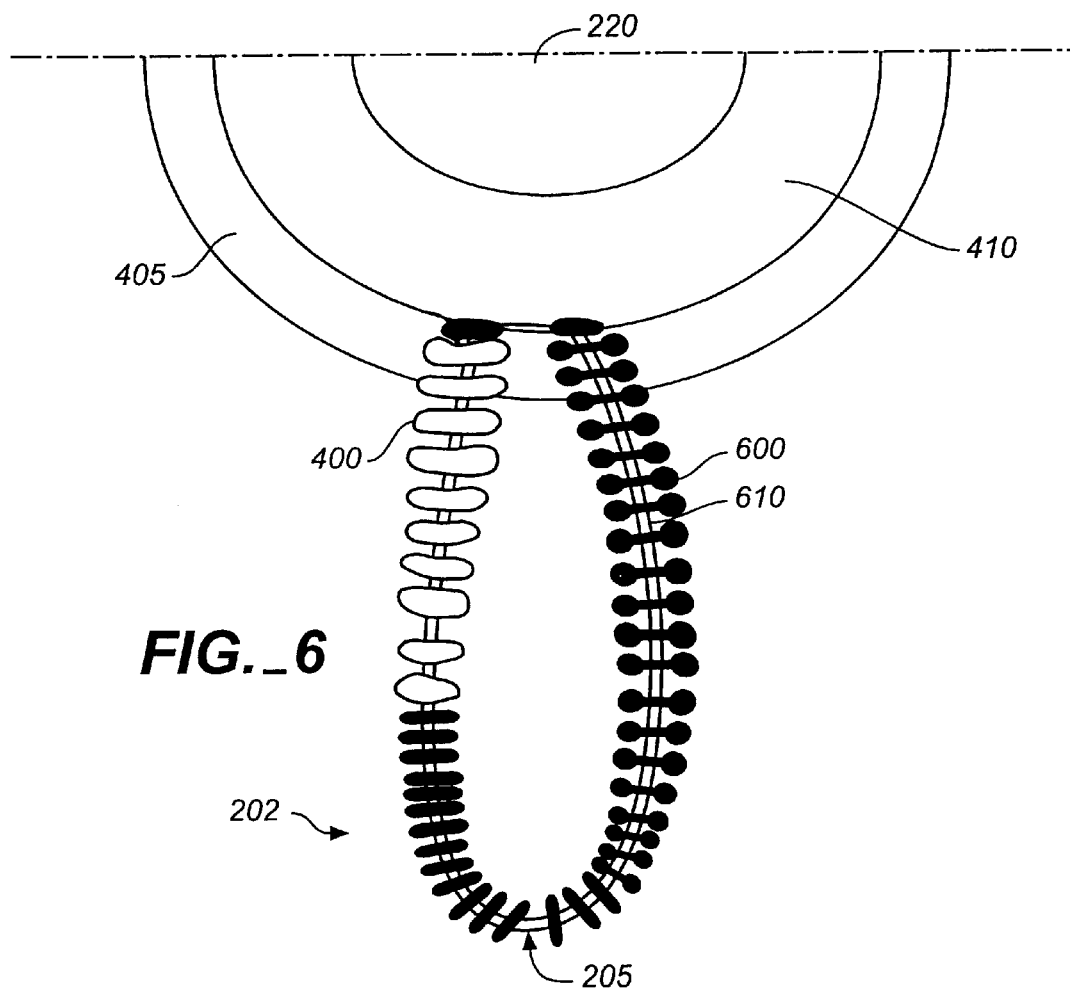
FIG._6

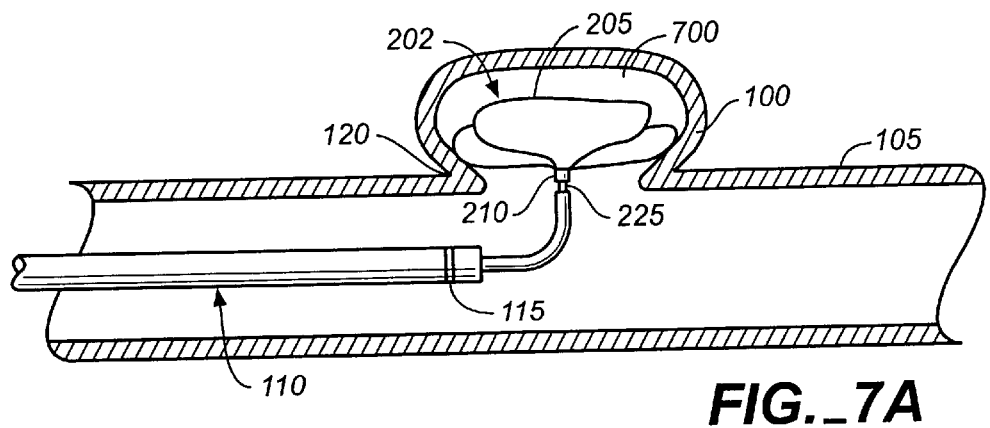
FIG._7A
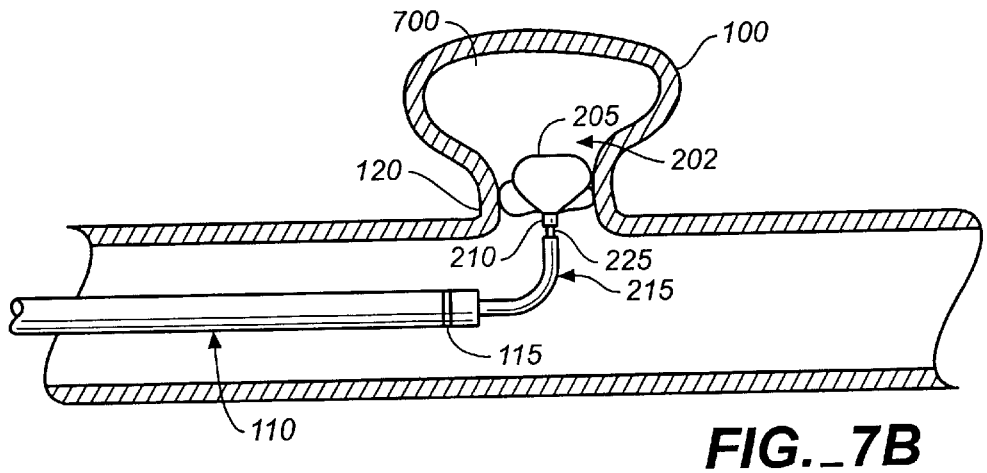
FIG._7B
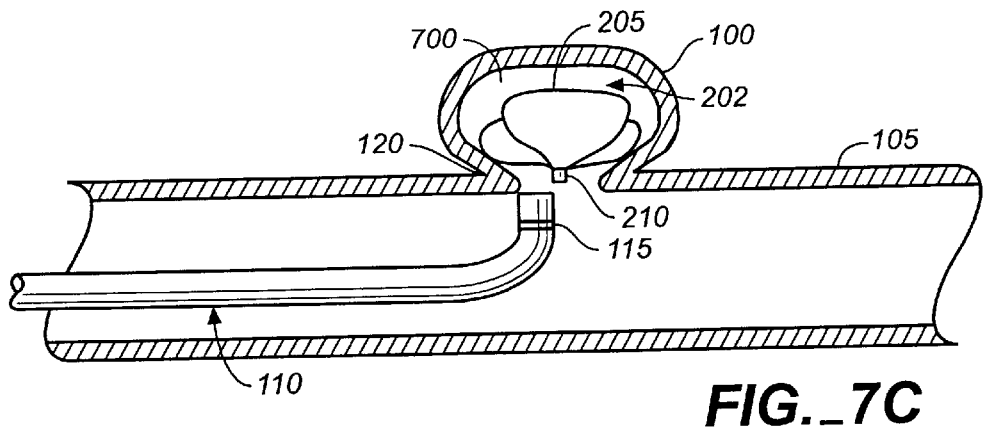
FIG._7C

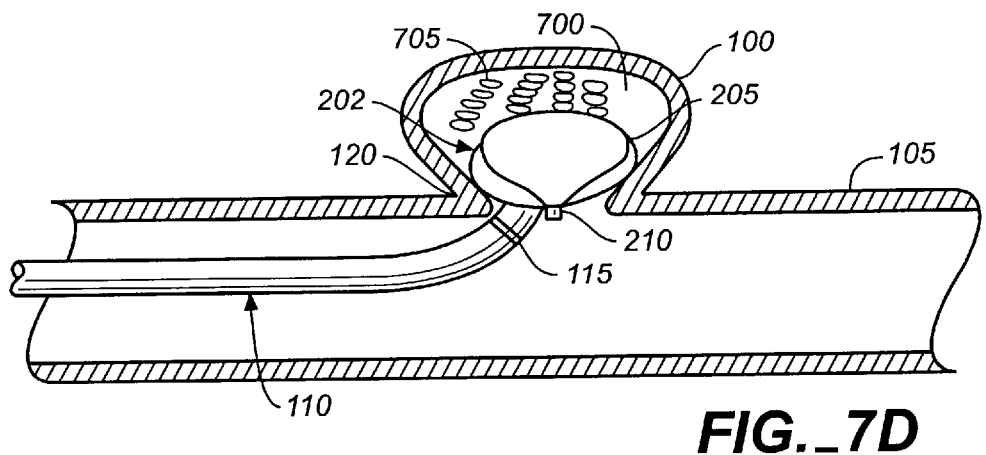
FIG._7D
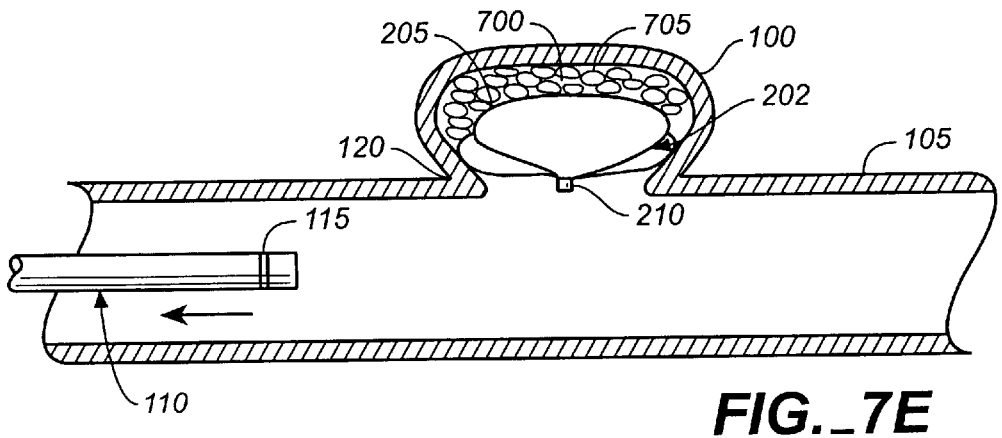
FIG._7E
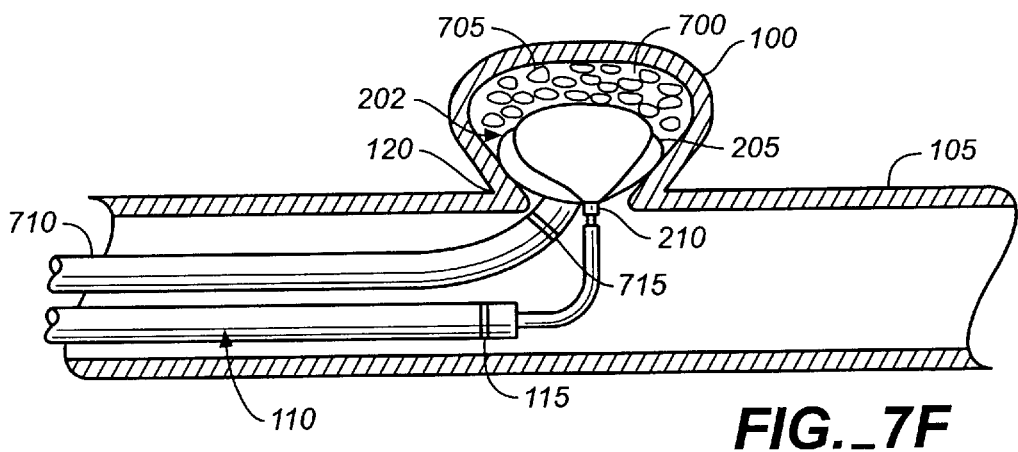
FIG._7F

BIOACTIVE THREE LOOP COIL

RELATED APPLICATIONS

This is a continuation-in-part of U.S. application Ser. No. 09/352,188, filed on Jul. 12, 1999 now U.S. Pat. No. 6,231,590, which is a continuation-in-part of U.S. application Ser. No. 09/189,540 filed on Nov. 10, 1998, now U.S. Pat. No. 6,187,024.

BACKGROUND OF THE INVENTION

The present invention deals with implantable medical devices. While conceivably the devices could be utilized in the context of a variety of body spaces, the present description, for the sake of brevity, will often be described in the context of the treatment of vascular aneurysms. Accordingly, one aspect of the present invention deals with an implantable medical device for at least partially obstructing the neck portion of a vascular aneurysm.

Another aspect of the present invention pertains to a medical device for forming an embolism within the vasculature of a patient. More particularly, it is a vaso-occlusion device at least partially coated with a bioactive agent, a collagenous material, or a collagenous coating optionally containing or coated with other bioactive agents. A highly flexible vaso-occlusive device coated with such materials also forms a variation of the invention.

Vascular aneurysms are typically formed due to a weakening in the walls of an artery. Often aneurysms are the site of internal bleeding and, catastrophically, the site of strokes. Different implantable medical devices have been developed for treating vascular aneurysms. Treatments commonly known as "artificial vaso-occlusion" treatments are known to be useful in treating aneurysms by filling associated undesirable vascular spaces. A variety of different vaso-occlusive devices are known to be at least arguably effective for the treatment of aneurysms.

Vaso-occlusive devices are surgical implants that are placed within open sites in the vasculature of the human body. The devices are introduced typically via a catheter to the site within the vasculature that is to be closed. That site may be within the lumen of a blood vessel or perhaps within an aneurysm stemming from a blood vessel.

There are a variety of materials and devices that have been used to create emboli in the vasculature of the human body. For instance, injectable fluids such as microfibrillar collagen, various polymeric foams and beads have been used. Certain injectable fluid devices can be introduced through a catheter and are capable of forming a solid space-filling mass in a target location. Polymeric resins, particularly cyanoacrylate resins, have been used as injectable vaso-occlusive materials. Both the injectable gel and resin materials are typically mixed with a radio-opaque material to allow accurate siting of the resulted materials. Although some of these agents provide for excellent short-term occlusion, many are thought to allow vessel recanalization due to absorption of the agents into the blood. In addition, there are significant risks involved in use of a cyanocrylates, and similar materials, due to the potential for misplacement. Such misplacement can create emboli in undesired areas. Generally, injectable fluid occlusion devices are somewhat difficult, if not impossible, to retrieve once they are improperly placed.

In some instances, materials such as hog hair and suspensions of metal particles have been introduced into an aneurysm by those wishing to form occlusions. It is believed that these materials encourage natural cell growth within the sac portion of an aneurysm.

Several patents describe different deployable vaso-occlusive devices that have added materials designed to increase their thrombogenicity. For example, fibered vaso-occlusive devices have been described in a variety of patents assigned to Target Therapeutics, Inc., of Fremont, Calif. Vaso-occlusive coils having attached fibers are shown in U.S. Pat. Nos. 5,226,911 and 5,304,194, both to Chee et al. Another vaso-occlusive coil having attached fibrous materials is found in U.S. Pat. No. 5,382,259, to Phelps et al. The Phelps et al. patent describes a vaso-occlusive coil which is covered with a polymeric fibrous braid on its exterior surface. U.S. Pat. No. 5,658,308, to Snyder, is directed to a vaso-occlusive coil having a bioactive core.

To further increase occlusive properties and thrombogencity, a variety of vaso-occlusive devices have been treated with a variety of substances. For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (via passage through the catheter) and the coil assumes a relaxed configuration—which is better suited to occlude the vessel—once the device is so-placed. Ritchart et al. describes a variety of shapes. The secondary shapes of the disclosed coils include "flower" shapes and double vortices. The coils may be coated with agarose, collagen, or sugar.

U.S. Pat. No. 5,669,931, to Kupiecki, discloses coils that may be filled or coated with thrombotic or medicinal material. U.S. Pat. No. 5,749,894, to Engleson, discloses polymer-coated vaso-occlusion devices. U.S. Pat. No. 5,690,671 to McGurk discloses an embolic element which may include a coating, such as collagen, on the filament surface.

U.S. Pat. No. 5,536,274 to Neuss shows a spiral implant which may assume a variety of secondary shapes. Some complex shapes can be formed by interconnecting two or more of the spiral-shaped implants. To promote blood coagulation, the implants may be coated with metal particles, silicone, PTFE, rubber lattices, or polymers.

As has been alluded to above, advancements in the artificial occlusion of aneurysms have occurred due to the delivery and implantation of metal coils as vaso-occlusive devices.

Vaso-occlusion coils are generally constructed of a wire, usually made of a metal or metal alloy, which is wound into a helix. Most commonly, these coils are introduced in a stretched linear form through a catheter to the selected target site, such as a particular aneurysm. The vaso-occlusion coils typically assume an irregular shape upon discharge of the device from the distal end of the catheter. The coils may undertake any of a number of random configurations used to fill an aneurysm. In some instances, vaso-occlusion coils are adapted to assume a predetermined secondary shape designed to enhance the ability to fill undesirable vascular spaces.

A variety of vaso-occlusion coils and braids are known. Tungsten, platinum, and gold threads or wires are said to be preferred. Vaso-occlusion coils have a variety of benefits including that they are relatively permanent, they may be easily imaged radiographically, they may be located at a well defined vessel site, and they can be retrieved.

In some instances, particularized features of coil designs, such as specialized mechanisms for delivering vaso-occlusion coils through delivery catheters and implanting them in a desired occlusion site, have been described. Examples of categories of vaso-occlusion coils having specialized delivery mechanisms include pushable coils, mechanically detachable coils, and electrolytically detachable coils.

Pushable coils are commonly provided in a cartridge and are pushed or plunged from an engaged delivery catheter into an aneurysm. A pusher wire advances the pushable coils through and out of the delivery catheter into the site for occlusion.

Mechanically detachable vaso-occlusive devices are typically integrated with a pusher wire and are mechanically detached from the distal end of that pusher wire after exiting a delivery catheter.

A variety of mechanically detachable devices are also known. For instance, U.S. Pat. No. 5,234,437, to Sepetka, shows a method of unscrewing a helically wound coil from a pusher having an interlocking surface. U.S. Pat. No. 5,250,071, to Palermo, shows an embolic coil assembly using interlocking clasps that are mounted both on the pusher and on the embolic coil. U.S. Pat. No. 5,261,195, to Twyford et al., shows a pusher-vaso-occlusive coil assembly having an affixed, proximately extending wire carrying a ball on its proximal end and a pusher having a similar end. The two ends are interlocked and disengaged when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,297, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

Within electrolytically detachable vaso-occlusive devices, the vaso-occlusive portion of the assembly is attached to a pusher wire via a small electrolytically severable joint. The electrolytically severable joint is severed by the placement of an appropriate voltage on the core wire. The joint erodes in preference either to the vaso-occlusive device itself or to the pusher wire. In accordance with principles of competitive erosion, parts of the wire that are not intended to erode are often simply insulated to prevent such an electrolytic response caused by the imposition of the electrical current.

U.S. Pat. No. 5,354,295 and its parent U.S. Pat. No. 5,122,136, both to Guglielmi et al., describe an electrolytically detachable embolic device. That is to say that a joint between the pusher wire and the vaso-occlusive portion dissolves or erodes when an electrical current is applied to the pusher wire.

Some vaso-occlusive devices include specialized mechanical features and/or shapes. Various shaped coils have been described. For example, U.S. Pat. No. 5,624,461, to Mariant, describes a three-dimensional in-filling vaso-occlusive coil. U.S. Pat. No. 5,639,277, to Mariant et al., describes embolic coils having twisted helical shapes and U.S. Pat. No. 5,649,949, to Wallace et al., describes variable cross-section conical vaso-occlusive coils. A random shape is described, as well. U.S. Pat. No. 5,648,082, to Sung et al., describes methods for treating arrhythmia using coils which assume random configurations upon deployment from a catheter. U.S. Pat. No. 5,537,338 describes a multi-element intravascular occlusion device in which shaped coils may be employed. Spherical shaped occlusive devices are described in U.S. Pat. No. 5,645,558 to Horton. Horton describes how one or more strands can be wound to form a substantially hollow spherical or ovoid shape when deployed in a vessel. U.S. Pat. Nos. 5,690,666 and 5,718,711, by Berenstein et al., show a very flexible vaso-occlusive coil having little or no shape after introduction into the vascular space.

One type of aneurysm commonly known as a "wide-neck aneurysm" is known to present particular difficulty in the placement and retention of vaso-occlusive devices. Furthermore, vaso-occlusive devices, in particular, vaso-occlusion coils, lacking substantial secondary shape strength may be difficult to maintain in position within an aneurysm no matter how skillfully they are placed.

Vaso-occlusive devices are typically placed in an aneurysm in the following fashion. A micro-catheter is initially steered into or adjacent the entrance of an aneurysm, typically aided by the use of a steerable guide wire. The guide wire is then withdrawn from the micro-catheter and replaced by the vaso-occlusive device. The vaso-occlusive device is advanced through and out of the micro-catheter, desirably being completely delivered into the aneurysm. After, or perhaps, during, delivery of the device into the aneurysm, there is a specific risk that the device or a portion of the device might migrate out of the aneurysm entrance zone and into the feeding vessel. The presence of the device in the feeding vessel may cause the undesirable response of an occlusion in the feeding vessel. Also, there is a quantifiable risk that blood flow in the feeding vessel and the aneurysm may induce movement of the device further out of the aneurysm, resulting in a more developed embolus in the patent vessel.

As noted above, aneurysms present particularly acute medical risk due to the dangers associated with an inherently thin vascular wall. The utilization of vaso-occlusive devices to occlude an aneurysm without occluding the adjacent vasculature poses a special challenge. Methods that meet this challenge and still avoid undue risk of an aneurysm rupture are desirable. None of the above documents discuss vaso-occlusive devices such as those found below.

SUMMARY OF THE INVENTION

One aspect of the present invention pertains to an implantable medical device for at least partially obstructing a neck portion of a vascular aneurysm. The device includes an occlusion subassembly comprising a base section and at least one lateral protrusion fixedly attached to the base section. A therapeutic agent is disposed upon at least one portion of the occlusion assembly.

Another aspect of the present invention pertains to an implantable retainer bridge, deliverable through a vascular catheter, of a size and overall flexibility to lodge at the neck of a vascular aneurysm, and suitable for retaining at least a vaso-occlusive device in a vascular aneurysm. The retainer bridge includes an elongated tubular delivery member and a vaso-occlusion device retainer subassembly. The subassembly includes a base section and a plurality of loops having ends fixedly attached to the base section. The subassembly has a first delivery shape when within the vascular catheter and a second deployed shape when not within the vascular catheter. The base section is positioned coaxially about and adjacent to a distal end of the elongate tubular delivery member. The base section is detachable from the elongated tubular member upon severance of an electrolytically severable joint. The electrolytically severable joint is located between the subassembly and the elongated tubular delivery member and is severable upon application of a suitable current to the joint. A therapeutic agent is disposed upon at least one portion of at least one of the plurality of loops.

BRIEF DESCRIPTION OF THE DRAWINGS

FIG. 1 is a partial sectioned view of a catheter extending toward an aneurysm emanating from the wall of a blood vessel.

FIG. 2 is a side view of an implantable bridge assembly.

FIG. 3 is a partial sectioned view of the implantable bridge assembly inserted within the catheter.

FIG. 4 is a partial sectioned view of the implantable bridge assembly.

FIG. 5 is an end view, taken along line 2A in FIG. 2, of the implantable bridge assembly.

FIG. 6 is a detailed end view of a lateral protrusion portion of the implantable bridge assembly.

FIGS. 7A to 7F are partial sectioned views of the aneurysm and illustrate procedural elements associated with using the implantable bridge assembly.

DETAILED DESCRIPTION OF THE ILLUSTRATIVE EMBODIMENTS

Figure 8:
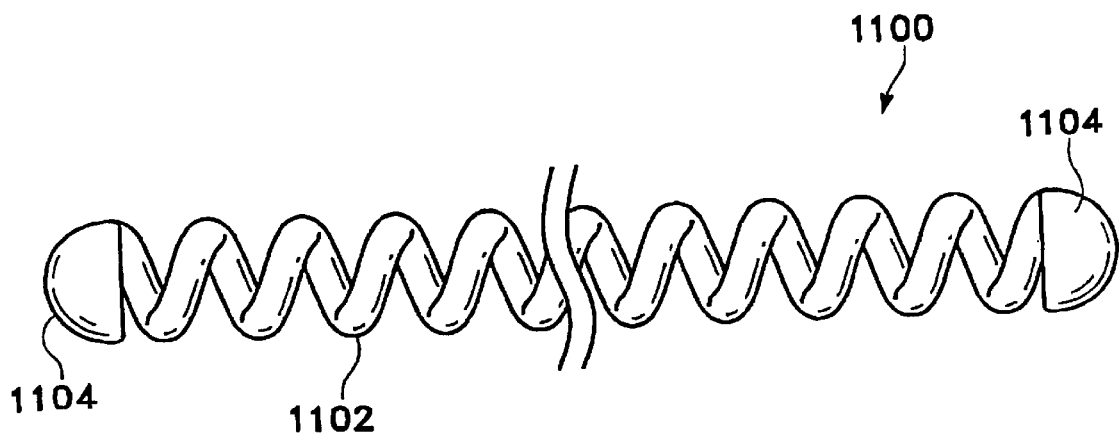
FIG. 8 is a perspective view of one embodiment of the invention.

FIG. 1 illustrates a partial sectioned view of an aneurysm 100 emanating from the wall of a feeding vessel 105. A catheter 110 is shown having a radio-opaque band 115 at its distal end. As is known in the art, radio-opaque band 115 assists in the guidance of catheter 110 through a vascular system utilizing principles of radiography or fluoroscopy. As illustrated, the distal end of catheter 110 has been guided so as to extend through a neck portion 120 of aneurysm 100.

FIG. 2 illustrates a side view of an implantable retainer bridge assembly 200 in accordance with one aspect of the present invention. Assembly 200 includes a plurality of lateral protrusions 205, which are fixedly connected to a base section 210. In accordance with one embodiment, base section 210 is a central tubular member. Lateral protrusions 205 in combination with base section 210 make up a bridge subassembly 202. While lateral protrusions 205 are illustratively wire loops, other types of lateral protrusions should be considered within the scope of the present invention. For example, lateral protrusions 205 could be formed as a plurality of non-looping arms extending from base section 210. In addition, while FIG. 2 illustratively includes three lateral protrusions 205, more or fewer lateral protrusions could be utilized.

Retainer assembly 200 further includes a core wire 215 (also know as a pusher wire) having a distal end 220 which includes a severable joint 225. Bridge subassembly 202, more particularly, base section 210, is fixedly connected to distal end 220 of core wire 215 and is positioned just distally of severable joint 225. In accordance with one embodiment, as will be described below, the bridge subassembly is directly connected to a portion of severable joint 225.

Retainer assembly 200 is deliverable through a tubular member such as catheter 110 in FIG. 1. The shape of retainer assembly 200 shown in FIG. 2 is the secondary shape or deployed shape found after the assembly has been pushed from a distal end of catheter 110. As retainer assembly 200 is pushed through catheter 110, it generally has a relatively retracted or low profile shape, which can be referred to as the delivery shape or primary shape. The delivery shape is essentially the shape of the interior of catheter 110.

FIG. 3 is an illustration of retainer assembly 200 in the delivery shape, as it is being delivered through catheter 110. The same reference numbers are used in FIG. 3 for elements that are the same or similar to those elements illustrated in FIGS. 1 and 2. After deployment from catheter 110, retainer assembly 200 assumes its secondary shape as is seen in FIG. 2. To undergo such massive changes in shape, lateral protrusions 205 are typically produced of material such as a super-elastic alloy. Super-elastic and pseudo-elastic shape recovery alloys and shape memory polymers (i.e., urethanes) are well known in this art. These alloys are especially suitable for lateral protrusions 205 because of their capacity to elastically recover—almost completely—to an initial configuration once stress is removed. In addition to super-elastic and pseudo-elastic alloys, other materials having shape memory characteristics are within the scope of the present invention.

Severable joint 225 (FIGS. 2 and 3) may also be called a sacrificial link. Severable joint 225 includes means for severing bridge subassembly 202 from most, if not all, of core wire 215. In one embodiment of the present invention, bridge subassembly 202 is directly and fixedly connected to a distal portion of severable joint 225, enabling a complete severance of subassembly 202 from core wire 215. In another embodiment, subassembly 202 is fixedly connected to a small portion of core wire 215 (distally located from joint 225) that remains with subassembly 202 following severance of joint 225. For example, the small portion of core wire 215 might, following severance, be substantially contained within base portion 210 of subassembly 202.

The severing action of joint 225, as will be described in greater detail below, enables subassembly 202 to remain in a portion of aneurysm 100 (FIG. 1) after most or all of core wire 215 and catheter 110 have been removed from feeding vessel 105. In accordance with one illustrative embodiment, severable joint 225 causes severance via mechanical means. Other means, however, should be considered within the scope of the present invention.

For the purpose of simplifying description, it will be assumed that severable joint 225 is an electrolytic severable joint. It should be noted that the Figures reflect this embodiment of the present invention. In accordance with the embodiment, as will be described in greater detail in relation to FIG. 4, core wire 215 is coated with an electrical insulator that is not susceptible to dissolution via electrolysis in blood or other ionic media. Severable joint 225 is not coated with such insulator and is constructed of a material that is susceptible to electrolytic dissolution in blood. Severable joint 225 is also significantly more susceptible to electrolytic dissolution than base section 210 and lateral protrusions 205 (bridge subassembly 202). In accordance with one embodiment, lateral protrusions 205 are attached to base section 210 but are not in an electrically conductive relationship therewith, and further, are coated with an electrical insulator that is not susceptible to dissolution via electrolysis in blood or other ionic media. In accordance with one aspect of the present invention, in response to an electrolytic control signal, only severable joint 225 dissolves, such that bridge subassembly 202 is severed from core wire 215. As was described above, subassembly could be directly connected to a portion of severable joint 225 or, alternatively, base section 210 of subassembly 202 could be fixedly connected to a small portion of core wire 215 (distally located from joint 225) that remains with subassembly 202 following severance of joint 225.

FIG. 4 is a partial sectional view of an embodiment of an implantable bridge assembly similar to the one illustrated in FIG. 2. The same reference numbers are used in FIG. 4 for elements that are the same or similar to those illustrated in previously described embodiments. It should be noted that the severable joint 225 within the FIG. 4 embodiment is illustratively consistent with the electrolytic severance embodiment described above. As was previously mentioned, other severance methods could be utilized.

In FIG. 4, implantable bridge assembly 200 includes lateral protrusions 205 that each illustratively include an attached marker coil 400. Marker coils 400 are illustratively constructed of radio-opaque material (i.e., platinum) that assists in the guidance of bridge subassembly 202 through a tubular delivery device (such as catheter 110 in FIG. 1) and through a vascular system, utilizing principles of radiography or fluoroscopy. In particular, marker coils 400 assist in the positioning of bridge subassembly 202 within an aneurysm, such as aneurysm 100 (FIG. 1). Bridge assembly 200 also includes base section 210 that comprises an outer marker coil 405 and an inner marker coil 410. In accordance with illustrative embodiments of the present invention, either, neither or both of outer marker coil 405 and inner marker coil 410 could be constructed of a radio-opaque material. As was previously described, such material assists in the guidance of subassembly 202 through a vascular system and into a target aneurysm.

Continuing with the description of FIG. 4, lateral protrusions 205 each illustratively include a plurality of ends 415 that are fixedly secured between outer marker coil 405 and inner marker coil 410. Other means for securing lateral protrusions 205 to base section 210 should be considered within the scope of the present invention. Inner marker coil 410 is adapted to radially surround and fixedly secure the most distal point of core wire 215. In another embodiment (not illustrated), as was described above, inner marker coil 410 could be adapted to fixedly connect to a distal portion of severable joint 225. In accordance with the electrolytic severance embodiment of severable joint 225, core wire 215 is covered with an insulation material 425 such that severable joint 225 is the only completely exposed portion of core wire 215. As was discussed above, this encourages the electrolytic severabilty of severable joint 225 when an electrolytic control signal is applied to assembly 200. Finally, retainer assembly 200 includes an optional marker coil 420 enclosed within insulation material 425. Optional marker coil 420 is constructed of a radio-opaque material (i.e., platinum) to provide further assistance in the location and precise placement of bridge subassembly 202 within a vascular system.

FIG. 5 is an end view of an embodiment of a bridge subassembly 202 portion of an implantable bridge assembly 200 similar to those illustrated in FIGS. 2 and 4. The FIG. 5 end view represents a view taken along line 2A in FIG. 2. The same reference numbers are used in FIG. 5 for elements that are the same or similar to those elements illustrated in previously described embodiments.

As is illustrated, retainer sub-assembly 202 includes lateral protrusions 205, a base section 210 and distal end 220 of core wire 215. In accordance with another embodiment, as was described above, base section 210 could alternatively be fixedly secured to a distal portion of a severable joint 225. Base section 210 further comprises inner marker coil 410 and outer marker coil 405. The plurality of ends 415 associated with lateral protrusions 405 are illustratively fixedly secured between outer maker coil 410 and inner marker coil 405.

FIG. 6 is an end view illustration of one particular lateral protrusion 205, in accordance with an illustrative embodiment of the present invention. Any of the lateral protrusions 205 described in relation to other embodiments of the present invention could be configured similar to the FIG. 6 embodiment described below. The same reference numbers are used in FIG. 6 for elements that are the same or similar to those illustrated in previously described embodiments.

Lateral protrusion 205 illustrated in FIG. 6 includes an interior wire 610 having an attached marker coil 400. Details pertaining to marker coil 400 were described above in relation to FIG. 4. Lateral protrusion 205 further includes a suture material 600 wrapped or braided around a portion of interior wire 610 that is not covered by marker coil 400. While FIG. 6 illustratively shows all of interior wire 610 covered either by marker coil 400 or suture material 600, some portions of wire 610 could, in accordance with one embodiment of the present invention, be exposed. In addition, additional suture material 600 could, in accordance with another embodiment, be attached to any portion of bridge subassembly 202 (i.e., attached to inner coil 410 or outer coil 405). Suture material 600 could, in accordance with yet other embodiments, also be attached to the distal end 220 of core wire 215 (FIG. 2), to an exposed portion of a joint 225 or to marker coils 400.

Suture material 600 is illustratively a therapeutic agent. In accordance with one embodiment, suture material 600 is or contains a bioactive material, such as a drug, protein, or genectic material, useful for the medical treatment of an aneurysm or other medical disorder. In accordance with another embodiment, suture material 600 is a bioactive material of a different type, such as a material selected or designed to encourage cell growth within a vascular aneurysm. In accordance with this embodiment, the material could illustratively be a natural bio-material, such as collagen, gelatin, fibrin, fibronectin, fibrinogen, hyaluronic acid, polysaccharides, or proteoglycans, or any combination thereof; or a combination of natural bio-materials and synthetic absorbable materials. In accordance with another embodiment, suture material 600 is constructed of a material that encourages cell growth within a targeted portion of an aneurysm, and is biologically absorbed by the human body. While there are many materials within the scope of the present invention that could be utilized as suture material 600, two that are biologically absorbable and designed to encourage cell growth are polylactic acid (PLA) and polyglycolic acid (PGA). In accordance with one embodiment, a mixture or composite composition comprising PLA and PGA could be utilized. Other potential suture materials that may encourage cell growth include polymers containing e-caprolactone, trimethylene carbonate, and p-dioxanone. The suture materials presently listed are only examples of the many potential materials that should be considered within the scope of the present invention.

Suture material 600 could be applied to any or all portions of bridge subassembly 202 in accordance with a variety of methods, all of which are embodiments of the present invention. Illustratively, suture material 600 is replaced by a material having a substantially liquid form which is sprayed on subassembly 202 or applied using a dip coating procedure. In that embodiment, the entire subassembly 202 can be coated with the therapeutic agent. Of course, suture material 600 or other forms of the therapeutic agent can be applied to substantially any portion of subassembly 202.

In addition, some materials suitable for use as suture material 600 (such as polylactic acid, polyglycolic acid or a mixture thereof) are available in extruded or molded forms. Extruded or molded materials such as these can be formed into desired shapes and applied to any portion of bridge subassembly 202. In accordance with one embodiment of the present invention, the material is formed into a tubular form and slipped over a portion of subassembly 202, such as over a portion of the wire forming a lateral protrusion 205. In accordance with another embodiment, as is illustrated in FIG. 6, the material is formed into a solid or strand form and is wrapped or braided around portions of bridge subassembly 202. In accordance with yet another embodiment, the material is heated and wrapped or braided around a mandrel having a desired shape (i.e., having a curvature consistent with a portion of subassembly 202). After the wrapped or braided material has cooled, it is removed from the mandrel and then has a permanent relaxed shape convenient for application to a bridge subassembly 202.

FIGS. 7A–7F are a series of partial sectioned views of an aneurysm 100 emanating from the wall of a feeding vessel 105. The same reference numbers are used in FIGS. 7A–7F for elements that are the same or similar to those illustrated in previously described embodiments. FIGS. 7A–7F illustrate procedural elements associated with using an implantable bridge assembly consistent with the present invention, as has been described in relation to the above described illustrative embodiments.

In accordance with the present invention, as is represented by FIG. 1, catheter 110 is initially steered into or adjacent to the entrance of an aneurysm, typically aided by the use of a steerable guide wire (not illustrated). As was discussed above in relation to FIG. 1, radio-opaque band 115 may be used to assist in the steering of catheter 110 through a vascular system.

When catheter 110 has been positioned relative to an aneurysm, the guide wire is removed. As was discussed in relation to FIG. 3, implantable bridge assembly 200 is then pushed through catheter 110 so that bridge subassembly 202 exits a distal end of catheter 110 and takes on a deployed shape (similar to FIG. 2) within aneurysm 100. FIG. 7A illustrates subassembly 202 in the deployed shape within aneurysm 100. In accordance with the embodiment of FIG. 7A, subassembly 202 is positioned such that lateral protrusions 205 extend into a sac portion 700 of aneurysm 100.

FIG. 7B illustrates an alternate placement of a deployed subassembly 202 within an aneurysm 100. In accordance with the FIG. 7B embodiment of the present invention, subassembly 202 is positioned such that lateral protrusions 205 engage neck portion 120 of aneurysm 100. Depending on characteristics of the aneurysm being treated, particularly depending on the size of neck portion 120, either of the embodiments illustrated in FIGS. 7A and 7B may be most appropriate.

It should be noted that marker coil devices, such as marker coils 400, inner coil 410, outer coil 405 and optional coil 420, described above in relation to FIG. 4 could be utilized to steer and position subassembly 202 with an aneurysm. In accordance with an embodiment of the present invention, any or all of these radio-opaque markers could be utilized by an operator of the present implantable medical device to provide steering capability utilizing principles of radiography or fluoroscopy.

After bridge subassembly 202 is placed within a portion of aneurysm 100, the next step is to sever the subassembly from pusher wire 215. This severance occurs as described above in relation to the description of severable joint 225. In accordance with one embodiment, severable joint 225 dissolves in response to an electrolytic signal being applied thereto, thereby disengaging subassembly 202 from all or most of core wire 215. FIG. 7C is an illustration of bridge subassembly 202 engaged within aneurysm 100 after joint 225 has been severed.

After joint 225 has been severed, core wire 215 is removed from catheter 110. In accordance with one embodiment of the present invention, catheter 110 is then withdrawn, leaving subassembly 202 bridging neck 120 of aneurysm 100. As was described in relation to FIG. 6, in accordance with one embodiment of the present invention, subassembly 202 includes an attached suture material or other form that serves as a therapeutic agent for the treatment of aneurysm 100. In accordance with one embodiment, as was described above, the therapeutic agent is a biologically absorbable material that first encourages cell growth in the neck 120 portion of aneurysm 100 and then is biologically absorbed. Accordingly, subassembly 202 is capable of serving as a device for at least partially obstructing the neck 120 portion of an aneurysm. In accordance with another embodiment, as was also described above, the suture material on subassembly 202 simply serves as a drug delivery agent.

In accordance with one aspect of the present invention, bridge subassembly 202 can be utilized to retain vaso-occlusive devices, such as vaso-occlusion coils, within an aneurysm. Accordingly, as is illustrated in FIG. 7D, after core wire 215 has been removed from catheter 110, the distal end of catheter 110 is then engaged with an opening in bridge subassembly 202. Next, vaso-occlusive devices, illustratively vaso-occlusion coils 705, are pushed through catheter 110 into aneurysm 100. Then, as is illustrated by FIG. 7E, catheter 110 is removed from feeding vessel 105 and subsequently from the vascular system. Of course, in accordance with another embodiment of the present invention, coils 705 can be placed in the aneurysm 100 through a separate delivery catheter after placing subassembly 202 but prior to detaching it. FIG. 7F is an illustration of this latter embodiment wherein coils 705 are transported through a catheter 710 that is independent of catheter 110.

Regardless of the method of implantation, the implanted subassembly 202 illustratively includes an attached suture material that encourages cell growth in the neck 120 portion of aneurysm 100. Accordingly, subassembly 202, in combination with the attached suture material, serves as a retaining device for retaining vaso-occlusion coils 705 within aneurysm 100. In accordance with one embodiment, as described above, the suture material is biologically absorbable. In accordance with another embodiment of the present invention, vaso-occlusive devices are delivered before severance of severable joint 225 through a hollow core wire 115 and through an opening within base section 210 of bridge subassembly 202.

Another aspect of the present invention pertains to a vaso-occlusive device having an outer coating of a collagen-based material or other bioactive material. It may have other functional drugs or proteins associated (chemically linked or physically mixed) with the collagen. The collagen-based material is for the purpose of enhancing the rate and density of the occlusion produced by the vaso-occlusive device at the selected body site and specifically to promote permanent cellular in-growth at that site. The therapeutics, drugs, or proteinaceous material associated with the collagenous material are placed in the collagen to provide specific effects outlined below.

As used, the outer, collagen-based or other bioactive-based coating is preferably placed over an inner tie layer coating or treatment. The binding layer preferably provides a layer contiguous to the vaso-occlusive device and the outer coating. The inner coating is generally bonded to the vaso-occlusive member. The inner coating may be of know silane coupling agents or primer polymer agents (e.g., low molecular weight polymer adhesives) or the like. The inner coating may also be deposited on the member by plasma treatment or may simply be a plasma treatment of the type intended to etch the substrate. The inner coating may also include vapor-deposited polymers, e.g., polyxyxylene and the like. Other methods for applying the thin polymeric inner coating, e.g., by dripping or spraying dilute polymeric solution, may also be employed.

Preferably, the inner coating is permanently bonded to the coil and either chemically or physically bonded to the outer coating so that shortly after coil deployment, the outer material can safely perform its intended purposes, i.e. beginning the healing cascade within the vessel.

Another suitable tie layer coating involves "plasma treatment" of coils. (See, e.g., co-pending U.S. Ser. No. 08/598, 325). These plasma-treated coils exhibit an amino-functionality which may be measured using known chemical methods. When the devices treated by this process are placed in the bloodstream, the amino-functionality results in a slight positive ionic charge on the surface of the fibers. This amino-functionality attracts platelets and thrombogenic proteins from the bloodstream. Plasma treatment may be carried out using e.g., a plasma generator such as that found in U.S. Pat. No. 3,847,652. The plasma may comprise a nitrogen-containing gas, preferably those containing diatomic nitrogen or ammonia. Gas pressures are advantageously maintained at a very low level, e.g., no greater than about 5 millimeters of mercury, preferably from 0.1 to 2 millimeters of mercury.

The period of time in which the vaso-occlusive device is subjected tot he plasma need not be great. That is to say that for most applied power settings below about 200 watts and in the radio frequency region between 1 and 50 megaHertz, the time of reaction need not be greater than 10 minutes to achieve the results described herein.

Other plasma treating steps which are intended to etch the substrate are also suitable for this invention.

Figure 9:
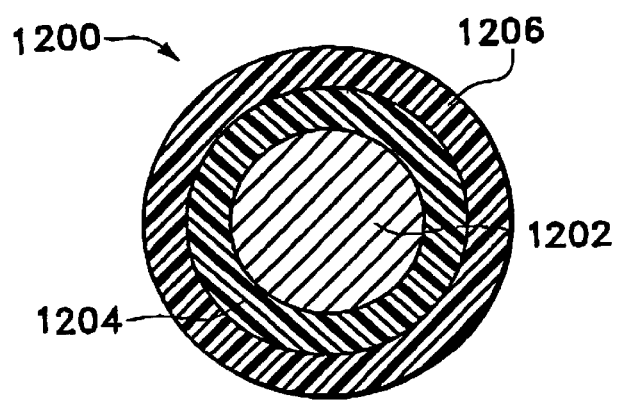
FIG. 9 is a perspective view of another embodiment of the invention showing a coil having a permanently bonded inner coating of a thrombotic agent and a water-soluble, dissolvable outer coating of an anti-thrombotic agent.

FIGS. 8 and 9 show typical vaso-occlusive devices suitable for use with this procedure. FIG. 8 shows a typical vaso-occlusive device 1100. Vaso-occlusive device 1100 is shown in FIG. 8 to include a helically wound coil 1102 having tips 1104 to ease the potential of the component wire to cause trauma in a blood vessel. The device may include tufts or fiber bundles attached to it, so as to increase the amount and volume of fiber held by the coil and thereby to promote overall thrombogencity of the device. Typical of a vaso-occlusive device comprising a helical coil having attached fibrous elements such as shown in FIG. 8 is found in U.S. Pat. No. 5,226,911, to Chee et al., the entirety of which is incorporated by reference.

FIG. 9 shows a vaso-occulsive device 1200 comprising a helically wound coil 1202, an inner tie coating 1204 and an outer collagenous coating 1206. The inner coating is generally a substance, preferably proteinaceous, which is bound to the coil 1202 and which is also bound, physically or chemically, to the outer collagenous covering 1206.

The occlusion devices of the invention may be made using conventional equipment and procedures. For example, helical coils may be prepared by wrapping a suitable wire about a cylindrical or conical mandrel. The stand(s) are then placed axially through the core of the helix and, if a multiplicity of strands are employed, their ends may be bound by heat, adhesives, or mechanical means. Radial filaments may be attached to the windings of the helix by tying or with adhesives.

The polymeric materials used in the vaso-occlusive devices in FIG. 8 and FIG. 9 are known materials. They are those materials which are generally approved for use as implants in the body or could be so approved. They may be of polymers such as polyethylene, polypropylene, polyvinylchloride, polyamides such as Nylon, polyurethanes, polyvinylpyrrolidone, polyvinyl alchohols, polyvinylacetate, cellulose acetate, polystyrene, polytetrafluoroethylene, polyesters such as polyethylene terphthalate (Dacron), silk, cotton, and the like. When the polymers are fibrous, they are often looped or tufted as shown in the drawings. Although it is not critical to this invention, they are usually assembled in bundles of 5 to 100 fibers per bundle. Preferred materials for the polymer component of vaso-occlusive devices comprise polyesters, polyethers, polyamides, and polyfluorocarbons. Especially preferred is polyethyleneterephthalate, sold as Dacron. Placing a protein-based covering on the fibers is a variation of the invention.

Another variation of the invention includes the specific use of polymers which evince an angiogenic response, preferably, biodegradable polymers, that are associated with the vaso-occlusive support base. By "associated" is meant that the material is tied to or is made to adhere to the vaso-occlusive support base. The composition may be a fabric or gauze-like structure. It may also be a non-woven or loose agglomeration of individual fibers. In general, they need to stay in place during the placement of the device in the body.

Preferably, the associated covering is a polymeric material such as a biodegradable polymer, e.g., polyglycolic acid, polylactic acid, reconstituted collagen, poly-p-dioxanone, and their copolymers such as poly(glycolide-lactide) copolymer, poly(glycolide-trimethylene carbonate) coplymer, poly(glycolide-$\epsilon$-caprolactone) copolymer, glycolidetrimethylene carbonate triblock copolymer, and the like. Mixtures of the noted polymers, e.g., of polylactide and polyglycolide may also be used. The associated coverings may also be used in conjunction with the bioactive coatings discussed elsewhere.

The coils (1102 in FIG. 8 and 1202 in FIG. 9) may be made of any of a wide variety of biocompatible metals or polymers or carbon. In particular, the metals may be selected from gold, rhenium, platinum, palladium, rhodium, ruthenium, various stainless steels, tungsten, and their alloys, titanium/nickel alloys particularly nitinoltype alloys. The preferred alloy is one comprising upwards of 90 percent platinum and at least a portion of the remainder, tungsten. This alloy exhibits excellent biocompatibility and yet has sufficient strength and ductility to be wound into coils of primary and secondary shape and will retain those shapes upon placement of the vaso-occlusive device in the human body. The diameter of the wire typically making up the coils is often in a range of 0.005 and 0.050 inches. The resulting primary coil diameter typically is in the range of 0.008 and 0.085 inches. Smaller coil diameters are used for finer problems and larger coil diameters and wire diameters are used in larger openings in the human body. A typical coil primary diameter is 0.015 and 0.018 inches. The axial length of a vaso-occlusive device may be between 0.5 and 100 centimeters. The coils are typically wound to have between 10 and 75 turns per centimeter.

In addition to the coils shown in the Figures, the vaso-occlusive device may comprise a substrate comprising a woven braid rather than the helical coil shown in those Figures. The vaso-occlusive device may comprise a mixture of the coil and braid. Indeed, it is within the scope of this invention that a portion of the coil be polymeric or a combination of metal and polymer.

It is further within the scope of this invention that the vaso-occlusive device comprise shapes or structures other than coils or braids, for example, spherical structures and the like.

In one aspect of the present invention, the vaso-occlusive devices described above and those similar to those specifically described above, are first optionally treated with a tie layer coating and then subjected to treatment to provide the outer collagenous, proteinaceous, or bioactive material layer. Preferably, neither the inner nor outer coating interfere with the shape of the coil after deployment. In one variation of the invention, the outer layer is applied to the vaso-occlusive base without the inner tie layer, but is applied in such an amount that the resulting assembly is not significantly more stiff than is the vaso-occlusive device without the covering. That is to say, the coated device is not more than 35%, preferably not more than 15%, and most preferably not more than 5%, stiffer than is the untreated device base. Preferably, the covering is less than about 1.0 mil, more preferably less than about 0.5 mil in thickness.

When a collagen layer, the outer collagenous layer may be of a wide variety of types, natural or synthetic, but preferably comprises a phot-polymerizable collagen which will bind both with the inner tie layer and with the added bioactive agents. The preferred collagenous materials have the same surface functional groups as to Type I and Type IV natural collagens. Those functional groups are typically of the type which bind to acrylate-type linkages.

The outer collagenous or proteinaceous coating may further contain additional materials which have one or more functions, including, but not limited to, reducing friction, providing a therapeutic for local or blood borne delivery, or enhancing thrombosis, coagulation, or platelet activity. The additional materials may be applied either as a substantially pure layer over the collagenous layer or chemically bonded to (and interspersed with) the collagenous layer or physically bonded tot he outer collagenous layer. The added bioactive materials may be, e.g., genes, growth factors, biomolecules, peptides, oligonucleodites, members of the integrin family, RGD-containing sequences, oligopeptides, e.g., fibronectin, laminin, vitronectin, hyaluronic acid, silk-elastin, fibrogenin, and other basement membrane proteins with bioactive agents.

Non-limiting examples of bioactive coating or materials suitable in this invention include both natural and synthetic compounds, e.g., fibrinogen, other plasma proteins, growth factors (e.g., vascular endothelial growth factor, "VEGF"), synthetic peptides of these and other proteins having attached RGD (arginine-glycine-aspartic acid) residues generally at one or both termini, or other cell adhesion peptides, i.e., GRGDY, oligonucleodides, full or partial DNA constructs, natural or synthetic phospholipids, or polymers with phosphorylcholine functionality.

Other bioactive materials which may be used in the present invention include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, naked DNA, cDNA, Rna, DNA, cDNA, or RNA in a non-infectious vector or in a viral vector which may have attached peptide targeting sequences; anti-sense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application, including retrovirus, adenovirus, adeno-associated virus, herpes simplex virus, and the like. For example, biologically active solutes include anti-thrombogenic agents such as heparin, heparin derivatives, urokinase, PPACK (dextrophenylalanine proline arginine chloromethylketone), rapamycine, probucol, and verapimil; angiogenic and anti-angiogenic agents; anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-mitotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Arg chloromethyl keton, and RGD peptide-containing compound, herparin, antithrombin compounds, platelet receptor antagonists, anti-thrombin anticodies, antiplatelet receptor antibodies, asprine, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factors inhibitors, growth factor receptor antagonists, transcriptional repressors, translational repressors, replication inhibitors, inhibitory antibodies, antibodies directly against growth factors, bifunctional molecules consisting of a growth factor and a cytotxin, bifunctional molecules consisting of an antibody and a cytotoxin; cholesterol-lowering agents; vasodilating agent; agents which interfere with endogenous vascoactive mechanisms, and combinations thereof. These and other compounds are applied to the stenting device.

Polynucleotide sequences useful in practice of the invention include DNA or RNA sequences having a therapeutic effect after being taken up by a cell. Examples of therapeutic polynucleotides include anti-sense DNA and RNA; DNA coding for an endogenous molecules. The polynucleotides of the invention can also code for therapeutic polypeptides. A polypeptide is understood to be any translation production of a polynucleotides regardless of size, and whether glycosylate or not. Therapeutic polypeptides include as a primary example, those polypeptides that can compensate for defective or deficient species in an animal, or those that act through toxic effects to limit or remove harmful cells from the body. In addition, the polypeptides or proteins that can be incorporated into the polymer coating 130, or whose DNA can be incorporated, include without limitation, proteins competent to induce angiogenesis, including factors such as, without limitation, acidic and basic fibroblast growth factors, vascular endothelial growth factor (including VEGF-2, VEGF-3, VEGF-A, VEGF-B, VEGF-C) hif-1 and other molecules competent to induce an upstream or downstream effect of an angiogenic factor; epidermal growth factor, transforming growth factor alpha and beta, platelet-derived endothelial growth factor, platelet-derived growth factor, tumor necrosis factor alpha, hepatocyte growth factor and insulin like growth factor; growth factors; cell cycle inhibitors including CDK inhibitors; thymidine kinase ("TK") and other agents useful for interfering with cell proliferation, including agents for treating malignacies; and combinations thereof. Still other useful factors, which can be provided as polypeptides or as DNA encoding these polypeptides, including monocyte chmoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP15, and BMP-16. Currently preferred BMP's are any of BMP-2, BMP-3, BMP-4, BMP-5, BMP-6, and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

In one exemplary embodiment of the present invention, the medical device has recombinant nucleic acid incorporated therein, wherein the recombinant nucleic acid comprises a viral vector having linked thereto an exogenous nucleic acid sequence. "Exogenous nucleic acid sequence" is used herein to mean a sequence of nucleic acids that is exogenous to the virus from which the vector is derived. The concentration of the viral vector, preferably an adenoviral vector, is at least about $10^{10}$ plaque forming units ("p.f.u."), preferably at least about $10^{11}$ p.f.u. Alternatively, the concentration of the viral vector is limited by the concentration that results in an undesirable immune response from a patient.

Treatment of vaso-occlusive coils with the described materials may be carried out using known methods, for example dip coating, spray coating, wiping, vapor deposition or the like.

The devices that are treated according to the procedure of this invention are often introduced to a selected site using the procedure outlined below. This procedure may be used in treating a variety of maladies. For instance, in treatment of an aneurysm, the aneurysm itself may be fill with the devices made according to the procedure specified here. Shortly after the devices are placed within the aneurysm, an emboli begins to form and, at some later time, is at least partially replaced by cellular material formed around the vaso-occlusive devices.

In general, a selected site is reached through the vascular system using a collection of specifically chosen catheters and guide wires. It is clear that should the aneurysm be in a remote site, e.g., in the brain, methods of reaching this site are somewhat limited. One widely accepted procedure is found in U.S. Pat. No. 4,994,069 to Ritchart, et al. It utilizes a fine endovascular catheter such as found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as the described in the Engelson patent are then placed through the guiding catheter as a unit. Once the tip of the guidewire reaches the end of the guiding catheter, it is then extended using fluoroscopy, by the physician to the site to be treated using the vaso-occlusive devices of this invention. During the trip between the treatment site and the guide catheter tip, the guidewire is advanced for a distance and the neurovascular catheter follows. Once both the distal tip of the neurovascular catheter and the guidewire have reached the treatment site, and the distal tip of that catheter is appropriately situated, e.g., within the mouth of an aneurysm to be treated, the guidewire is then withdrawn. The neurovasuclar catheter then has an open lumen to the outside of the body. The devices of this invention are then pushed through the lumen to the treatment site. They are held in place variously because of their shape, size, or volume. These concepts are described in the Ritchart et al. patent as well as others. Once the vaso-occlusive devices are situated in the vascular site, the embolism forms.

Although the present invention has been described with reference to preferred embodiments, workers skilled in the art will recognize that changes may be made in form and detail without departing from the spirit and scope of the invention.

What is claimed is:

1. An implantable medical device for at least partially obstructing a neck portion of a vascular aneurysm, comprising:

an occlusion subassembly comprising a base section and at least one lateral protrusion fixedly attached to the base section;

a therapeutic agent disposed upon at least one portion of the occlusion subassembly, the therapeutic agent being a bioactive material, the bioactive material being a biologically absorbable suture material that encourages cell growth.

2. The implantable medical device of claim 1, wherein the biologically absorbable suture material is polylactic acid.

3. The implantable medical device of claim 1, wherein the biologically absorbable suture material is polyglycolic acid.

4. The implantable medical device of claim 1, wherein the biologically absorbable suture material is a mixture of polyglycolic acid and polylactic acid.

5. The implantable medical device of claim 1, wherein the biologically absorbable suture material is polylactic acid.

6. The implantable medical device of claim 1, wherein the biologically absorbable suture material is polyglycolic acid.

7. The implantable medical device of claim 1, wherein the biologically absorbable suture material is a mixture of polyglycolic acid and polylactic acid.

8. An implantable medical device for at least partially obstructing a neck portion of a vascular aneurysm, wherein the implantable medical device is of a size and overall flexibility to lodge at the neck portion of the vascular aneurysm and is deliverable through a tubular delivery device, the device comprising:

an occlusion subassembly comprising a base section and at least one lateral protrusion fixedly attached to the base section, wherein said at least one lateral protrusion is a plurality of loop members that extend radially from the base section and include a plurality of ends that are fixedly attached to said base section;

a therapeutic agent disposed upon at least one portion of the occlusion subassembly, wherein the therapeutic agent is a bioactive material, and wherein the bioactive material is a biologically absorbable suture material that encourages cell growth.

9. The implantable medical device of claim 8, wherein the biologically absorbable suture material is polylactic acid.

10. The implantable medical device of claim 8, wherein the biologically absorbable suture material is polyglycolic acid.

11. The implantable medical device of claim 8, wherein the biologically absorbable suture material is a mixture of polyglycolic acid and polylactic acid.

12. The implantable medical device of claim 8, wherein the biologically absorbable suture material is further disposed upon at least one portion of the base section.

13. The implantable medical device of claim 12, wherein the biologically absorbable material is sprayed on at least one portion of the base section and at least one portion of at least one lateral protrusion.

14. The implantable medical device of claim 12, wherein the biologically absorbable material is dip coated on at least one portion of the base section and at least one portion of at least one lateral protrusion.

15. The implantable medical device of claim 8, wherein the biologically absorbable suture material is produced in a strand form and wrapped around at least one portion of at least one lateral protrusion.

16. The implantable medical device of claim 8, wherein the biologically absorbable suture material is produced in a strand form and braided around at least one portion of at least one lateral protrusion.

17. The implantable medical device of claim 8, wherein the biologically absorbable material is produced in a tubular form and slipped over at least one portion of the occlusion subassembly.

18. The implantable medical device of claim 8, wherein the biologically absorbable material is sprayed on at least one portion of the occlusion subassembly.

19. The implantable medical device of claim 8, wherein the biologically absorbable material is dip coated on at least one portion of at least one lateral protrusion.

20. An implantable retainer bridge, deliverable via a vascular catheter, of a size and overall flexibility to lodge at the neck of a vascular aneurysm, and suitable for retaining at least a vaso-occlusive device in a vascular aneurysm, comprising:

an elongated tubular delivery member having a proximal end and a distal end;

a vaso-occlusion device retainer subassembly comprising a base section, a plurality of loops having ends fixedly attached to said base section, said retainer subassembly having a first delivery shape when within said vascular catheter and a second deployed shape, different than the first delivery shape, when said retainer subassembly is not retained within said vascular catheter, said base section being positioned coaxially about and adjacent to the distal end of said elongate tubular delivery member, said base section being detachable from said elongated tubular member upon severance of an electrolytically severable joint;

said electrolytically severable joint being between said retainer subassembly and said elongated tubular delivery member, severable upon application of a suitable current to said joint; and a therapeutic agent disposed upon at least one portion of at least one of the plurality of loops, wherein the therapeutic agent is a bioactive material, and wherein the bioactive material is a biologically absorbable suture material that encourages cell growth.

21. The implantable retainer bridge of claim 20, wherein the biologically absorbable suture material is further disposed upon at least one portion of the base section.

22. The implantable retainer bridge of claim 21, wherein the biologically absorbable material is sprayed on at least one portion of the base section and at least one portion of at least one of the plurality of loops.

23. The implantable retainer bridge of claim 21, wherein the biologically absorbable material is dip coated on at least one portion of the base section and at least one portion of at least one of the plurality of loops.

24. An implantable retainer, deliverable via an elongate tubular delivery device, for retaining at least a vaso-occlusive device in a vascular aneurysm, comprising:

a core wire having a proximal end and a distal end;

a joint extending between the distal end of the core wire and at least one array element, said joint being electrolytically severable upon application of a suitable current to said joint, said joint being comparatively more susceptible to electrolytic severability than said core wire and said at least one array element;

a retainer assembly comprising said at least one array element, said retainer assembly having a first delivery shape when retained within said elongate tubular delivery device and a second deployed shape, different than the first delivery shape, when said retainer assembly is not retained within said tubular delivery device, said at least one array element extending outwardly from said joint in said second deployed shape, and wherein after an electrolytic severance from said core wire, said retainer assembly includes a residual joint; and bioactive material disposed upon at least one portion of at least one array element, wherein the therapeutic agent is a bioactive material, and wherein the bioactive material is a biologically absorbable material.

25. The implantable retainer of claim 24, wherein the biologically absorbable suture material is polylactic acid.

26. The implantable retainer of claim 24, wherein the biologically absorbable suture material is polyglycolic acid.

27. The implantable retainer of claim 24, wherein the biologically absorbable suture material is a mixture of polyglycolic acid and polylactic acid.

28. An occlusion device for the medical treatment of a vascular aneurysm, comprising:

an aneurysm neck bridge that includes a protrusion that is attached to, and extends from, a hub; and a therapeutic agent disposed upon at least one portion of the aneurysm neck bridge.

29. The device of claim 28, wherein the therapeutic agent is a bioactive material.

30. The device of claim 29, wherein the bioactive material is a biologically absorbable suture material that encourages cell growth.

* * * * *